United States Patent [19]

Rosenblatt

[11] Patent Number: 4,799,925
[45] Date of Patent: Jan. 24, 1989

[54] ASPIRATOR FOR COLLECTION OF BODILY FLUIDS

[76] Inventor: Richard Rosenblatt, 304 S. Oakhurst Dr., Beverly Hills, Calif. 90212

[21] Appl. No.: 209,851

[22] Filed: Jun. 22, 1988

Related U.S. Application Data

[62] Division of Ser. No. 903,017, Sep. 2, 1986.

[51] Int. Cl.$^4$ .................................... A61M 5/00
[52] U.S. Cl. .................................... 604/181; 128/767; 128/768; 128/201.25; 128/202.29; 215/1 C; 215/6; 215/DIG. 3; 604/73; 604/118; 604/319
[58] Field of Search ............ 604/47, 50, 54, 73, 604/76, 118, 117, 128, 133, 181, 183, 185, 186, 264, 275, 276, 278, 313–321, 902; 128/750, 760, 762, 767, 768, 771, 201.25, 201.28, 202.29, 203.11, 205.18, 205.19, 202.29, 206.11, 206.22, 207.14, 207.16; 215/1 C, 6, 309, 320, DIG. 3

[56] References Cited

U.S. PATENT DOCUMENTS

| | | | |
|---|---|---|---|
| 3,018,779 | 1/1962 | Tyler et al. | 604/181 |
| 3,037,497 | 6/1962 | Roberson | 128/202.29 |
| 3,343,422 | 9/1967 | McSmith | 73/864.03 |
| 3,352,304 | 11/1967 | Bartlett, Jr. | 128/202.29 |
| 3,485,404 | 12/1969 | Newton | 604/319 |
| 4,196,808 | 4/1980 | Pardo | 215/6 |
| 4,273,126 | 6/1981 | Grane et al. | 604/319 |
| 4,275,724 | 6/1981 | Behrstock | 604/281 |
| 4,319,570 | 3/1982 | Grane | 604/317 |
| 4,397,643 | 8/1983 | Rygiel | 215/11 E |

FOREIGN PATENT DOCUMENTS

| | | | |
|---|---|---|---|
| 2934915 | 3/1981 | Fed. Rep. of Germany | 604/319 |
| 1563804 | 4/1980 | United Kingdom | 604/319 |

Primary Examiner—C. Fred Rosenbaum
Assistant Examiner—Mario Costantino
Attorney, Agent, or Firm—Thomas I. Rozsa

[57] ABSTRACT

An aspirator includes two closed containers with one container having a suction tube connected to a closed bellows within the container for creating a vacuum, and the second container having a patient tube for insertion into the body cavity of a patient for sucking removal of mucus and other excess bodily fluids by the vacuum, with the two containers being connected for gaseous communication.

30 Claims, 2 Drawing Sheets

U.S. Patent  Jan. 24, 1989  4,799,925
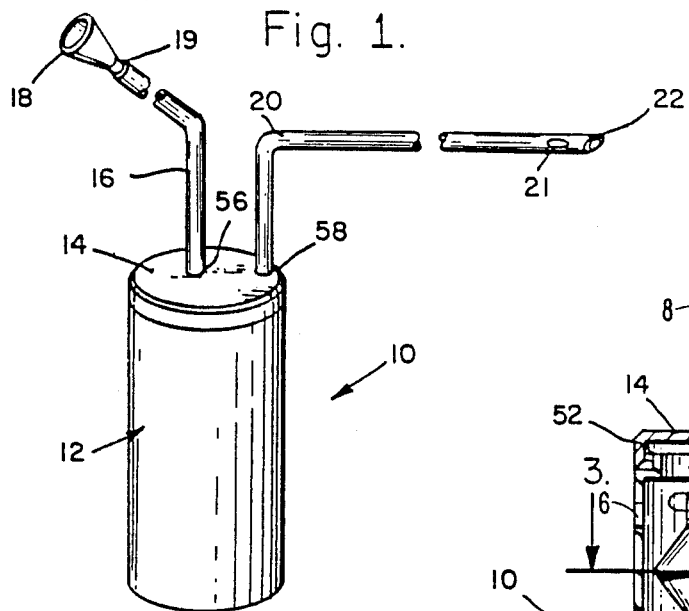
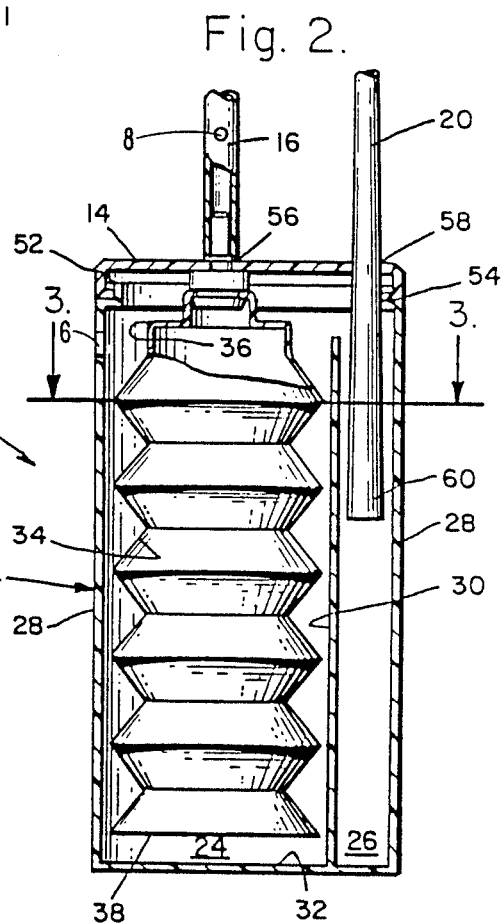
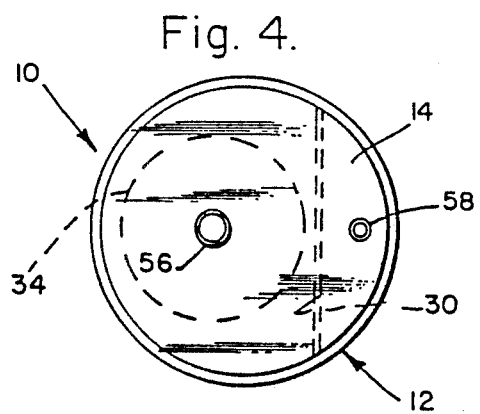
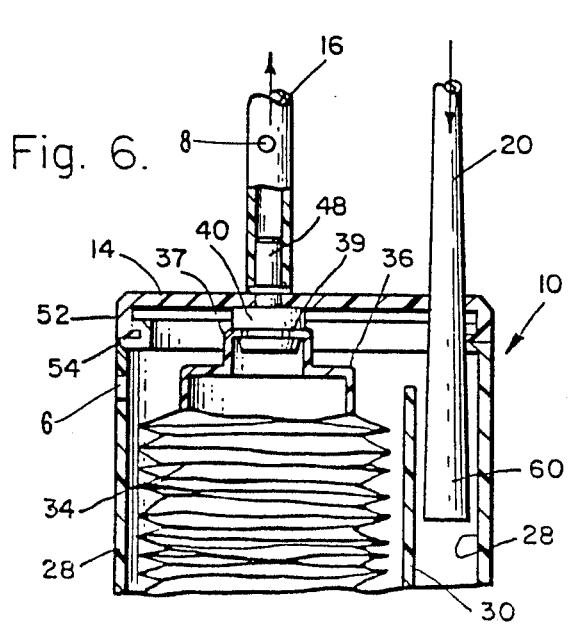
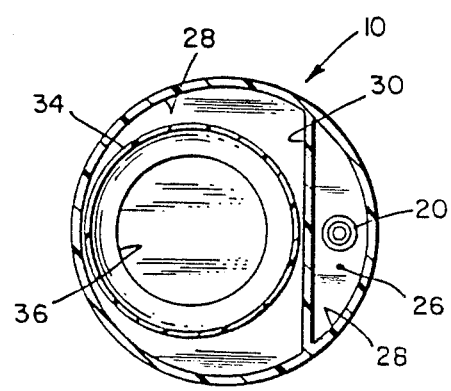

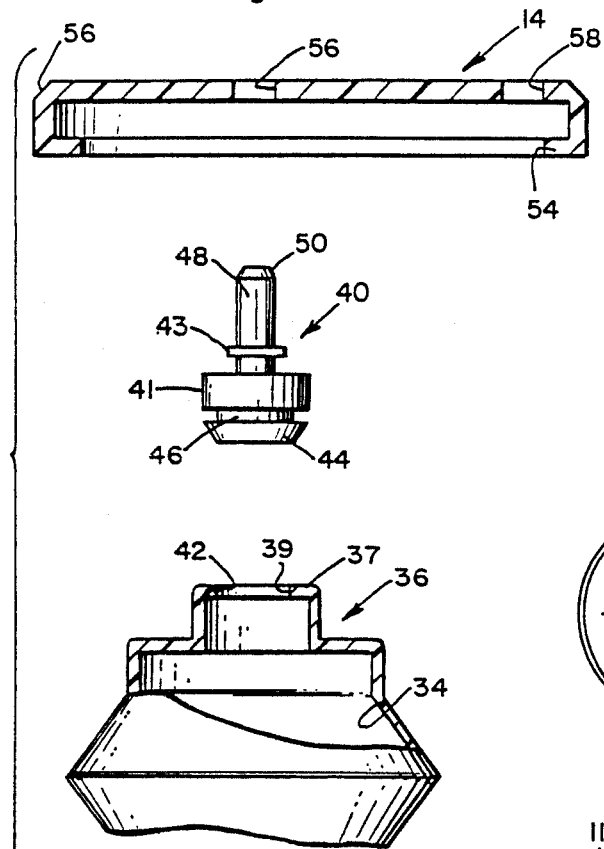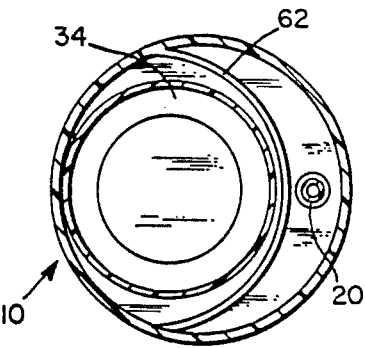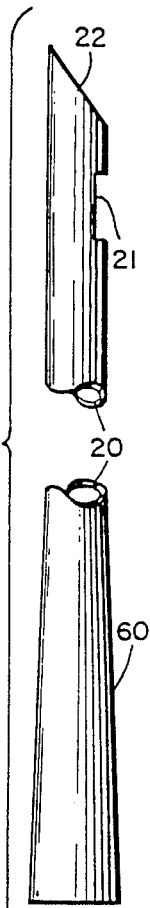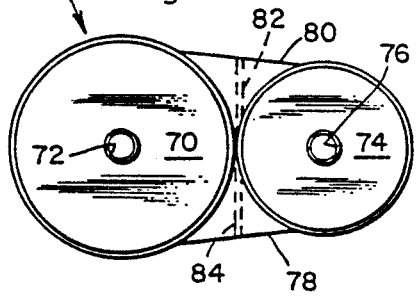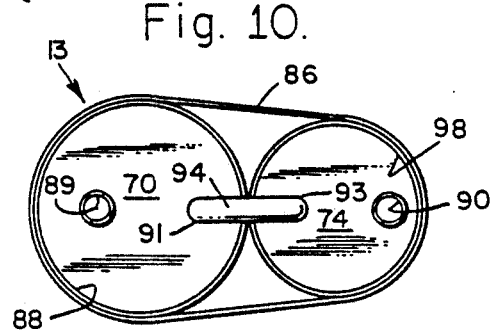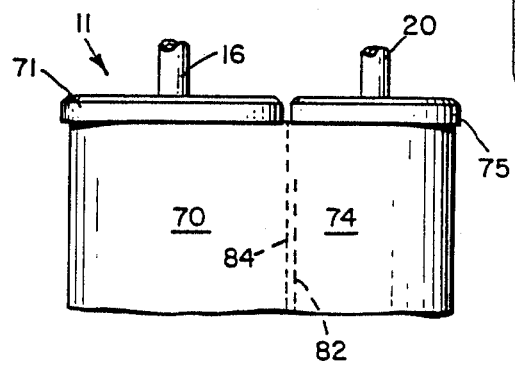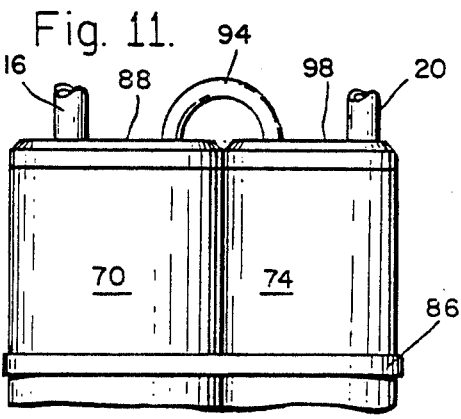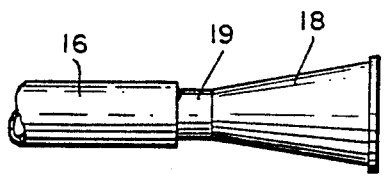

ASPIRATOR FOR COLLECTION OF BODILY FLUIDS

BACKGROUND OF THE INVENTION

This application is a Divisional Application of co-pending application Ser. No. 06/903,017 filed on 09/02/86 now U.S. Pat. No. 4,775,366.

1. Field of the Invention

The present invention relates to aspirators. More particularly, the present invention relates to an aspirator for removing bodily fluid from a body cavity, such as mucus from the mouth and throat, through oral suction by another person.

2. Description of the Prior Art

It is often necessary to remove bodily fluids, such as mucus and other matter, from the throat of a patient, especially in the case of newborn infants. Vacuum operated collection devices for collecting such bodily fluids are known in prior art.

Such collection devices generally include a container having a screw-on or snap-on cap that provides a fluid-tight closure, and a pair of tubes connected to nipples protruding from the cap in fluid communication with the interior of the container and with each other. In use, one of the tubes is connected to a source of vacuum or a suction force, for example, a mouthpiece for providing suction by mouth, or to another conventional source of hospital vacuum. The other tube may be inserted into the throat or other body cavity of the patient to permit withdrawal of fluid from the bodily cavity, and its collection in the container, in response to suction.

An example of this type of fluid collection device is found in U.S. Pat. No. 4,317,525, issued to Schuessler et al., which includes the improvement of including a weak portion in the wall adjacent the cap to facilitate removal of the cap. Such devices, however, allow air from the patient's body cavity to enter the suction tube, where bacteria or germs in it can contaminate and infect either a person who is sucking, or a hospital suction system.

Another such fluid collection system is disclosed in U.S. Pat. No. 3,084,691, to Stoner. Stoner includes a foot-operated bellows pump for creating suction in a collection chamber having two nipples and mating tubes attached thereto, with one of the nozzles being used to suck bodily fluids from a body cavity. The apparatus in Stoner is relatively large, bulky, complex and expensive. In addition, it does not provide any indication of the amount of resistance to the sucking, which provides important feedback to a person using the device, who can responsively apply only the suction necessary to remove the subject liquids. Finally, Stoner too allows commuciation of the air to the nurse from the patient through the pump.

While the prior art discloses bodily fluid collection devices relying on suction, such devices allow communication of air, and other gas from the patient through the device, and in the instance of a manually operated device, into the nurse or other health care provider. Although such devices do not normally allow liquid from the patient to enter into the suction system, they do allow air or other gas to enter into the suction tube and the source of vacuum, thereby increasing the danger of further spreading of communicable diseases.

Therefore, there is a significant need for a bodily fluid collection device that isolates both the liquid and the gas fluids extracted from a patient by the health care provider, through a suction apparatus.

SUMMARY OF THE INVENTION

Accordingly, it is an object of the present invention to provide a bodily fluid collection device that completely isolates gaseous and liquid fluids collected from the patient from the source of suction, which may conveniently be a person, such as a nurse.

It is a further object of the present invention to provide a bodily fluid collection device that is disposable.

It is a further object of the present invention to provide a bodily fluid collection device that is relatively inexpensive to manufacture.

It is a further object of the present invention to provide a bodily fluid collection device that is easy to open, thereby making the contents readily available for analysis.

It is a further object of the present invention to provide a disposable bodily fluid collection device that is sterile prior to use.

Accordingly, there is provided a container having a bottom wall and a sidewall, a top having two apertures therein, or the equivalent, such as two protruding nipples, removably attached to the container, a patient tube inserted through one of the apertures for insertion into a patient's body cavity, and a suction tube attached through the other aperture and having its remote end attached to a source of suction, which may be a person, or another conventional source of vacuum, and a means for transmitting a partial vacuum throughout the container and the patient tube without allowing fluid, that is, either gas or liquid, communication between the two tubes.

In a preferred embodiment, the vacuum transmitting means comprises a bellows that is expanded in its equilibrium or relaxed state, and that contracts in response to negative pressure, that is, in response to sucking on the suction tube, the suction tube being operatively connected to the bellows. In the preferred embodiment, the bellows is contained entirely within the container.

The invention may also include means for releasing air from the container during the relaxation cycle of the bellows, that is, means for permitting air to be exhausted from the container while the bellows expand without having the displaced air exhausted through the patient tube. This air releasing means may further comprise an aperture (6 as illustrated in FIG. 6) in the sidewall of the container, or in the sucking tube (aperture 8 as illustrated in FIG. 6) which is covered (for example by the operator) during sucking, and uncovered while the bellows is being restored to its equilibrium, that is, fully opened position.

Alternatively, the air releasing means may be automatic, and may include, for example, a ball valve seat disposed in the patient tube, preferably in the end of the patient tube that is contained within the container, the ball valve being forced closed during the relaxation or expansion cycle of the bellows, and drawn open during sucking, and a flap valve in the container, with the flap vale being naturally in the closed position during expansion of the bellows into its equilibrium position. Such air releasing means is not, however, necessary for proper and efficacious operation of the invention and may be too expensive for mass production of disposable aspirators.

Another feature of the preferred embodiment of the invention comprises an upstanding partition within the container, which is contiguous with the sidewall of the container along two lines and along the bottom wall, forming two chambers, which are a liquid collection chamber and a vacuum transmitting chamber, wherein said chambers are in gaseous communication, but not in liquid communication, because the upstanding partition does not extend to the top of the container. Plastic is a preferred material for making the container, the top and the nipple in the top for attaching the suction tube to the container. A nipple in the top of the container may also be used for attaching of the patient tube.

In a preferred embodiment, the container is cylindrical. The upstanding partition may be either straight, or arcuate. An arcuate upstanding partition is preferred because its use allows more efficient use of the space available within the container.

Other alternative embodiments utilize two separate containers, one for containing the bellows, and the other for collecting the bodily fluid, and a means for conducting gas from one container to another. Such means may include an externally disposed flexible tube connected to the top of each container, or an internal partition. In either case, the bodily fluid collection chamber is readily detachable from the vacuum generating chamber, for permitting easy access to the collected liquid, for medical testing.

Further novel features and other objects of the present invention will become apparent form the following detailed description, discussion, and the appended claims taken in conjunction with the drawings.

BRIEF DESCRIPTION OF THE DRAWINGS

Referring particularly to the drawings for the purpose of illustration only and not limitation, there is illustrated:

FIG. 1 is a perspective view of an aspirator according to the present invention.

FIG. 2 is a section elevation of an aspirator according to the present invention, illustrating the bellows in their relaxed, or equilibrium position.

FIG. 3 is a section of an aspirator according to the present invention, taken along lines 3-3 of FIG. 2.

FIG. 4 is a plan view of an aspirator according to the present invention, without the tubes attached to the top.

FIG. 5 is a section of a aspirator according to the present invention, corresponding to FIG. 3, but showing an aspirator having an arcuate internal upstanding partition.

FIG. 6 is a partial cross-sectional elevation of an aspirator according to the present invention illustrating the bellows in their contracted, that is vacuum-creating state.

FIG. 7 is an exploded side elevation, partially fragmentary, illustrating the cap, bellows, and suction tube fitting for the vacuum-creating portion of the apparatus.

FIG. 8 is a plan view of an alternative embodiment of an aspirator according to the present invention in which separate circular containers are employed.

FIG. 9 is a fragmentary elevation of the apparatus of FIG. 8.

FIG. 10 is a plan view of an alternative embodiment of an aspirator according to the present invention in which separate circular containers are employed, and are joined in gaseous communication by an external tube that penetrates the top of each container.

FIG. 11 is a fragmentary elevational view of the apparatus of FIG. 10.

FIG. 12 is a fragmentary elevational of the suction tube according to the present invention, including the mouthpiece.

FIG. 13 is an elevation of the patient tube adapted for use with the present invention, illustrating the uniform taper that lodges the patient tube into correct position within the aspirator, and the Murphy tip at the remote end for insertion into the body cavity to be drained.

DETAILED DESCRIPTION OF THE PREFERRED EMBODIMENT

Referring to FIG. 1, there is shown aspirator 10 having a cylindrical container 12, cap 14, suction tube 16, terminating in flared mouthpiece 18 which is a separate piece having nipple 19 which is inserted into suction tube 16, and patient tube 20, terminating in Murphy tip 22, all illustrated in perspective. Murphy tip 22 consists of cutting patient tube 20 at an oblique angle to present a more easily inserted surface, and providing aperture 21 adjacent to the tip, as is well-known in the art.

In the preferred embodiment illustrated in FIG. 1, suction tube 16 and patient tube 20 are made of a flexible, rubber-like material, typically rubber or a synthetic substitute, such as polyvinyl chloride or other material well known in the art. Cylindrical container 12 is preferably made of a hard plastic material, by means of injection or blow-molding, but may be made of any rigid material, such as metal or hard rubber. Aspirator 10 is preferably disposable and is about 5 centimeters in outside diameter and about 10 centimeters long.

In use, aspirator 10 is hung from the user's neck by a cord, so that aspirator 10 is at about mid-chest level, and mouthpiece 18 is inserted into the user's mouth. Murphy tip 22 of patient tube 20 is inserted into the body cavity to be drained, and then the user sucks on flared mouthpiece 18, creating a partial vacuum that is communicated through patient tube 20 to the patient, by means that will be described in greater detail below, thereby drawing liquid and other fluid from the body cavity of the patient. When used as described, aspirator 10 leaves both of the user's hands free, to hold the patient and manipulate patient tube 20. That is, the use of the hands is not required to hold or otherwise manipulate aspirator 10 or mouthpiece 18, a great advantage in using the present invention. When used in this fashion, the preferred length of suction tube 16 is approximately 20 to 30 centimeters, and the preferred length of patient tube 20 is about 30 to 40 centimeters.

Referring to FIG. 2, cylindrical container 12 comprises two internal chambers, vacuum creating chamber 24, and mucus trap 26, created by sidewall 28, and internal upstanding partition 30, which is integrally formed with sidewall 28 of cylindrical container 12 during molding, and is attached to bottom wall 32, as well as two lines of joinder with sidewall 28, as is best illustrated in FIG. 3. Internal upstanding partition 30 rises upward through most of the height of cylindrical container 12, preferably rising a distance within the range of one-third to seven eighths of the length of the container, but does not reach cap 14, thereby creating a path for communication of air and other gaseous fluid between vacuum creating chamber 24 and mucus trap 26.

Vacuum creating chamber 24 contains bellows 34, attached to bellows cap 36 by being integrally formed therewith, or attached by a suitable adhesive. Bellows 34 is preferably made from silicon rubber, having a thickness of from about 1 to about 1.5 millimeters. Silicon rubber is a material well known in the art of medical supplies and is also employed in such well known household items as baby bottle nipples. Silicon rubber has an excellent memory, which consistently restores an article formed from it to its original shape, if it is deformed and then the deforming force is removed. Therefore, no spring or other elastic member is required in bellows 34. Bellows 34 is preferably formed in a single unitary piece, having a sealed bottom 38 formed of the same material, by blow molding.

Referring to FIG. 7, there is most clearly illustrated the relationship between bellows 34, bellows cap 36, bellows stopper 40, and cap 14. Bellows cap 36 may conveniently be formed from hard rubber or the like and attached to the top of bellows 34 with a conventional adhesive. The top of bellows cap 36 comprises aperture 42 for receiving bellows stopper 40, made of pliable rubber or the like, and having a tapered nose section 44, for easing penetration of aperture 42, slot 46, circumferentially disposed about the base of bellows stopper 40, adjacent to tapered nose section 44, for further easing penetration of aperture 42 by bellows stopper 40 into bellows cap 36, and in which top wall 37 of bellows cap 34 is seated when bellows stopper 40 is inserted through aperture 39 of bellows cap 36.

Attached to the top of bellows stopper 40 and integrally formed therewith is nipple 48, for allowing attachment of suction tube 16. Central orifice 50 penetrates the entire length of bellows stopper 40, allowing gaseous communication from suction tube 16 to the interior of bellows 34.

Cap 14 includes depending circumferential skirt portion 52, which terminates in inwardly projecting circumferential lip 54, and includes suction tube aperture 56, and patient tube aperture 58, in its top portion.

Suction tube aperture 56 is penetrated by nipple 48 of bellows stopper 40 until cap 14 is sandwiched between base section 41 and flange 43 of bellows stopper 40. Mouthpiece 18, suction tube 16, bellows stopper 40, and bellows 34 thereby provide a closed system with mouthpiece 18 providing the only means of entry and exit of gas or other fluid into or out of bellows 34.

As best illustrated in FIGS. 2, 13, one end of patient tube 20 is disposed downward within mucus trap 26 of aspirator 1, at a distance in the range of about 3 to about 5 centimeters, or about one-third to about three-fourths of the length of the container, thereby insuring that mucus sucked into aspirator 10 falls into mucus trap 26, as long as aspirator 10 is in virtually any orientation other than upside down. Tapered portion 60 of patient tube 20 disposed within container 10 is uniformly tapered along the length intended to remain within aspirator 10, such that the diameter of tapered portion 60 of patient tube 20 is greater than the diameter of patient tube aperture 58.

Operation of aspirator 10 is clearly illustrated in FIGS. 2 and 3. Referring to FIG. 2, bellows 34 is shown in its relaxed state. When a user sucks on mouthpiece 18, bellows 34 is contracted by air pressure conducted through patient tube 20, into the interior of aspirator 10, through mucus trap 26, over internal upstanding partition 30, and into vacuum creating chamber 24, allowing bellows 34 to contract. Naturally, as bellows 34 contracts, air is drawn into aspirator 10. When Murphy tip 22 of patient tube 20 is lodged near or in mucus or other bodily fluids, these liquids and other fluids are drawn into mucus trap 26. Liquid falls to the bottom of mucus trap 26, while gas flows into vacuum creating chamber 24. Referring to FIG. 6, bellows 34 is illustrated in its contracted, or vacuum creating, state.

Naturally, when the medical care provider releases the sucking action from the mouthpiece 18, bellows 34 expands to its original position, as illustrated in FIG. 2, due to the memory of the silicon rubber material the bellows is made from. Expansion of bellows 34 naturally expels air from vacuum creating chamber 24, which can only be exhausted from aspirator 10 through patient tube 20. It has been found in practice that one suction cycle is usually sufficient to withdraw mucus and other liquids form the pertinent body cavity. If, however, more than one suction cycle is required, it has been found that allowing the air to be blown out through patient tube 20 into the body cavity being drained does not create any problems or difficulties. Hence, there is no real need for any type of valves that would prevent air from being blown out through patient tube 20.

Referring to FIG. 4, there is shown a plan view of aspirator 1 according to the present invention. Such an aspirator may include a straight line internal upstanding partition 30, as illustrated in FIGS. 2 and 3, or it may include an arcuate internal upstanding partition 62, as illustrated in FIG. 5, which better utilizes interior volume of aspirator 10, by allowing partition 62 to be closer to bellows 34, thereby allowing use of a smaller diameter cylindrical container 12.

Referring to FIG. 8, there is shown an alternative embodiment of aspirator 11 having separate vacuum creating chamber 70, including suction tube aperture 72, and mucus trap 74, including patient tube aperture 76. Vacuum creating chamber 70 having cap 71 and mucus trap 74 having cap 75 are joined by sidewalls 78, 80, which are both tangent to the cross-sectional circles of vacuum creating chamber 70 and mucus trap 74. Internal upstanding partition 82 isolates mucus and other bodily liquids in mucus trap 74 from contact with vacuum creating chamber 70, but does not reach to the top of aspirator 11, as was described in conjunction with FIGS. 1 through 7 above. Sidewalls 78, 80 include frangible score line 84, allowing aspirator 11 to be cleanly and easily broken along frangible score line 84, thereby separating mucus trap 74 from vacuum creating chamber 70, providing a smaller container for use in analysis of the mucus or other bodily liquid trapped in mucus trap 74.

Referring to FIGS. 10 and 11, there is shown another alternative embodiment of aspirator 10 according to the present invention, in which vacuum creating chamber 70 is a cylindrical container wholly separate from mucus trap 74, which are joined together by rubber band 86, or other suitable fastener. Tube 94 connects vacuum chamber 70 and mucus trap 74. Tube 94 is disposed outside aspirator 13 across the top of aspirator 13, which includes a separate vacuum chamber cap 88, and a separate mucus trap cap 98, each of which may be removable. Tube 94 may be inserted into aperture 91 of cap 88, and aperture 93 of cap 98. Alternatively, of course, nipples may be integrally formed in caps 88, 98 to receive tube 94.

A suction tube (not shown) may be attached at suction tube aperture 89 by any convenient means, such as those described above. A patient tube may be conveniently attached as described with reference to FIGS. 1-7 through patient tube aperture 90. In the embodiment illustrated in FIGS. 10, 11, vacuum chamber cap 88 is not removable, but it may be a removable cap like that of FIG. 7 if desired.

The embodiment illustrated in FIGS. 10, 11 allows easy and quick separation of vacuum creating chamber 70 from mucus trap 74, by removing rubber band 86 and removing the tube 94 from aperture 93. Mucus trap 74 can then be sealed by inserting a small stopper into each aperture of cap 98, and sent to the laboratory, where the contents can be analyzed to determine the cause of any medical problems the patient may be suffering. Mucus trap 74 of this embodiment has a separate mucus trap cap 98, having the depending circumferential skirt and inwardly projecting lip which allows mucus trap cap 98 to be removed from mucus trap 74 easily, as illustrated in FIG. 7. In other respects, especially regarding the bellows vacuum and fluid separation system described above, the embodiment of FIGS. 10, 11 operates the same as that shown and described in reference to FIGS. 1-7.

The embodiment illustrated in FIG. 10 is particularly preferred because it allows re-use of vacuum creating chamber 70 and bellows 34, which are the most expensive components of the system, while at the same time maintaining the separation of patient fluids from the medical care provider. If desired, aspirator 10 can be sterilized, particularly vacuum creating chambe 70, which will prevent spread of infection form one patient to another if the device is re-used.

In its preferred embodiment, however, aspirator 10 is disposable, and furthermore is sterile when shipped and is protected by sterile wrapping, thus insuring that bacteria or germs cultured from mucus trapped in mucus trap 74 is from the patient.

Referring to FIG. 12, there is illustrated suction tube 16, including flared mouthpiece 18 having nipple 19 for insertion into tube 16. Referring to FIG. 13, there is illustrated patient tube 20, including Murphy tip 22 having aperture 21, and tapered portion 60 for insertion upwardly through cap 14, or other cap or closure on mucus trap 26, 74, and so forth.

Of course, the present invention is not intended to be restricted to any particular form or arrangement, or any specific embodiment disclosed herein, or any specific use, since the present invention may be modified in various particulars or relations without departing from the scope of the claimed invention shown and described herein, of which the apparatus shown are intended only for illustration and for disclosure of operative embodiments and not to show all of the various forms or modifications which might embody the invention.

The invention has been described in considerable detail in order to comply with the patent laws by providing a full public disclosure of one of its forms. Such detailed description is not, however, intended in any way to limit the broad features or principles of the invention, or the scope of the patent property to be granted.

What is claimed is:

1. An aspirator for removing bodily fluids through human suction and subsequent collection of the removed bodily fluids, comprising:
   a. a vacuum creating container having a bottom wall, a side wall, and a top having a first aperture and a second aperture spaced apart from the first aperture therein;
   b. a mucus trap container having a bottom wall, a side wall and a top having a first aperture and a second aperture spaced apart from the first aperture therein;
   c. means for removably fastening said vacuum creating container and said mucus trap container together;
   d. a mating member comprising a housing having a central longitudinal passage extending through its length so as to provide two open ends in fluid communication with each other through said longitudinal passage, said mating member extending through said first aperture in the top of said vacuum creating container such that a first open end of the mating member protrudes through and above said top of said vacuum creating container and the second open end of the mating member extends into the vacuum creating container;
   e. a first hollow tube having two ends, with the first end attached to said first end of the mating member and the second end attached to a mouthpiece;
   f. a flexible bellows member comprising an integrally formed flexible bellows and terminating in a sealed bottom at one end and affixed to a bellows cap at its other end;
   g. said bellows cap further comprising an opening through which it is attached to the second end of said mating member to thereby provide a closed system permitting gaseous communication therethrough between the mouthpiece, the second hollow tube, the mating member and the bellows, and to further permit the flexible bellows to extend into said vacuum creating container such that the flexible bellows is in its fully expanded position when in its equilibrium state;
   h. a second hollow tube having two ends, with the first end inserted through said second aperture of said mucus trap container such that said second hollow tube extends for a distance inside the container and the second end extends for a distance beyond said top of said mucus trap container and further comprises at least one opening adjacent its tip; and
   i. a tube having two ends, with one end inserted into said second aperture in the top of said vacuum creating container and the other end inserted into said first aperture in the top of said mucus trap container, to thereby permit gaseous communication between the two containers;
   j. whereby in use, the second end of said second hollow tube is inserted into the patient from which bodily fluid is to be removed and the mouthpiece of the first hollow tube is sucked on by the person treating the patient, and suction through the mouthpiece will cause said flexible bellows to contract to thereby create a vacuum in the vacuum creating container which through gaseous communication with the mucus trap container causes air and bodily fluids from the patient to be sucked into and remain in the mucus trap container while the airtight system from the mouthpiece through the flexible bellows prevents any direct communication of air or bodily fluids between the patient and the person treating the patient.

2. An aspirator in accordance with claim 1 wherein said fastening means further comprises a rubber band.

3. An aspirator in accordance with claim 1 wherein said bellows is made of silicon rubber.

4. An aspirator in accordance with claim 1 wherein the length of said second hollow tubing proximate its first end includes a tapered end portion such that said second hollow tubing cannot be withdrawn upward through the top of said mucus trap container.

5. An aspirator in accordance with claim 1 wherein said vacuum creating container is circular and the top of said vacuum creating container further comprises a circular top having a circumferential depending skirt portion and an inwardly projecting circumferential lip attached to the bottom of said skirt.

6. An aspirator in accordance with claim 1 wherein said vacuum creating container and its top are made of a plastic material.

7. An aspirator in accordance with claim 1 wherein said mucus trap container is circular and the top of said mucus trap container further comprises a circular top having a circumferential depending skirt portion and an inwardly projecting circumferential lip attached to the bottom of said skirt.

8. An aspirator in accordance with claim 1 wherein said mucus trap container and its top are made of a plastic material.

9. An aspirator in accordance with claim 1 wherein said bellows comprises a unitary cylindrical bellows made of an airtight elastic membrane.

10. An aspirator in accordance with claim 1 further comprising means for permitting air to be exhausted from the vacuum creating container after the sucking action has ceased and while the bellows expand to its equilibrium state without having the displaced air exhausted through the second hollow tube.

11. An aspirator in accordance with claim 10 wherein said means for permitting air to be exhausted is an aperture in the sidewall of the vacuum creating container.

12. An aspirator in accordance with claim 10 wherein said means for permitting air to be exhausted is an aperture in the portion of said first hollow tube outside said vacuum creating container, whereby said aperture is covered during the sucking process and uncovered while the bellows is being restored to its equilibrium.

13. An aspirator in accordance with claim 1 wherein the second end of said second hollow tube terminates in a Murphy tip.

14. An aspirator in accordance with claim 1 wherein the top of said mucus trap container is removable from the sidewall of the mucus trap container.

15. An aspirator in accordance with Cl-aim 1 wherein the top of said mucus trap container is not removable from the sidewall of the mucus trap container.

16. An aspirator for removing bodily fluids through human suction and subsequent collection of the removed bodily fluids, comprising:
   a. a vacuum creating container having a bottom wall, a side wall, and a top having a first aperture and a second aperture spaced apart from the first aperture therein;
   b. a mucus trap container having a bottom wall, a side wall and a top having a first aperture and a second aperture spaced apart from the first aperture therein;
   c. means for removably fastening said vacuum creating container and said mucus trap container together;
   d. a flexible bellows member comprising an integrally formed flexible bellows and terminating in a sealed bottom at one end and affixed to a bellows cap containing an opening at its other end, said flexible bellows member located within the vacuum creating container when the device is assembled;
   e. a first hollow tube having two ends, with the first end inserted through said first aperture in the top of said vacuum creating container and further inserted through and retained by the opening in said bellows cap and the second end extending for a distance beyond said top and attached at its tip to a mouthpiece, to thereby provide a closed system permitting gaseous communication therethrough between the mouthpiece, the second hollow tube, the mating member and the bellows, and to further permit the flexible bellows to extend into said vacuum creating container such that the flexible bellows is in its fully expanded position when in its equilibrium state;
   f. a second hollow tube having two ends, with the first end inserted through said second aperture of said mucus trap container such that said second hollow tube extends for a distance inside the container and the second end extends for a distance beyond said top of said mucus trap container and further comprises at least one opening adjacent its tip; and
   g. a tube having two ends, with one end inserted into said second aperture in the top of said vacuum creating container and the other end inserted into said first aperture in the top of said mucus trap container, to thereby permit gaseous communication between the two containers;
   h. whereby in use, the second end of said second hollow tube is inserted into the patient from which bodily fluid is to be removed and the mouthpiece of the first hollow tube is sucked on by the person treating the patient, and suction through the mouthpiece will cause said flexible bellows to contract to thereby create a vacuum in the vacuum creating container which through gaseous communication with the mucus trap container causes air and bodily fluids from the patient to be sucked into and remain in the mucus trap container while the airtight system from the mouthpiece through the flexible bellows prevents any direct communication of air or bodily fluids between the patient and the person treating the patient.

17. An aspirator in accordance with claim 16 wherein said fastening means further comprises a rubber band.

18. An aspirator in accordance with claim 16 wherein said bellows is made of silicon rubber.

19. An aspirator in accordance with claim 16 wherein the length of said second hollow tubing proximate its first end includes a tapered end portion such that said second hollow tubing cannot be withdrawn upward through the top of said mucus trap container.

20. An aspirator in accordance with claim 16 wherein said vacuum creating container is circular and the top of said vacuum creating container further comprises a circular top having a circumferential depending skirt portion and an inwardly projecting circumferential lip attached to the bottom of said skirt.

21. An aspirator in accordance with claim 16 wherein said vacuum creating container and its top are made of a plastic material.

22. An aspirator in accordance with claim 16 wherein said mucus trap container is circular and the top of said mucus trap container further comprises a circular top having a circumferential depending skirt portion and an inwardly projecting circumferential lip attached to the bottom of said skirt.

23. An aspirator in accordance with claim 16 wherein said mucus trap container and its top are made of a plastic material.

24. An aspirator in accordance with claim 16 wherein said bellows comprises a unitary cylindrical bellows made of an airtight elastic membrane.

25. An aspirator in accordance with claim 16 further comprising means for permitting air to be exhausted from the vacuum creating container after the sucking action has ceased and while the bellows expand to its equilibrium state without having the displaced air exhausted through the second hollow tube.

26. An aspirator in accordance with claim 25 wherein said means for permitting air to be exhausted is an aperture in the sidewall of the vacuum creating container.

27. An aspirator in accordance with claim 25 wherein said means for permitting air to be exhausted is an aperture in the portion of said first hollow tube outside said vacuum creating container, whereby said aperture is covered during the sucking process and uncovered while the bellows is being restored to its equilibrium.

28. An aspirator in accordance with claim 16 wherein the second end of said second hollow tube terminates in a Murphy tip.

29. An aspirator in accordance with claim 16 wherein the top of said mucus trap container is removable from the sidewall of the mucus trap container.

30. An aspirator in accordance with claim 16 wherein the top of said mucus trap container is not removable from the sidewall of the mucus trap container.

* * * * *